(12) United States Patent
Osaki (10) Patent No.: US 10,085,623 B2
(45) Date of Patent: Oct. 2, 2018

(54) BENDING OPERATION APPARATUS OF ENDOSCOPE, AND ENDOSCOPE (71) Applicant: OLYMPUS CORPORATION, Tokyo (JP)

(72) Inventor: Itaru Osaki, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 15 days.

(21) Appl. No.: 15/260,503

(22) Filed: Sep. 9, 2016

(65) Prior Publication Data

US 2016/0374536 A1 Dec. 29, 2016

Related U.S. Application Data (63) Continuation of application No. PCT/JP2015/062843, filed on Apr. 28, 2015.

(30) Foreign Application Priority Data

Aug. 22, 2014 (JP) ................................. 2014-169441

(51) Int. Cl.
  *A61B 1/00* (2006.01)
  *A61B 1/005* (2006.01)
  *G02B 23/24* (2006.01)

(52) U.S. Cl.
  CPC .......... *A61B 1/0052* (2013.01); *A61B 1/0057* (2013.01); *G02B 23/2476* (2013.01)

(58) Field of Classification Search
  CPC ... A61B 1/00149; A61B 1/0016; A61B 1/005; A61B 1/0051; A61B 1/0052;

(Continued)

(56) References Cited

U.S. PATENT DOCUMENTS

| 5,402,793 A | 4/1995 | Gruner et al. |
| 5,762,067 A * | 6/1998 | Dunham ............. A61B 1/0052 600/148 |
| 2007/0005002 A1 * | 1/2007 | Millman ............ A61M 1/0058 604/30 |

FOREIGN PATENT DOCUMENTS

| EP | 0654245 A1 | 5/1995 |
| JP | 2005-040619 A | 2/2005 |

(Continued)

OTHER PUBLICATIONS

International Search Report dated Jul. 21, 2015 issued in PCT/JP2015/062843.

(Continued)

*Primary Examiner* — John P Leubecker
*Assistant Examiner* — Pamela F Wu
(74) *Attorney, Agent, or Firm* — Scully, Scott, Murphy & Presser, P.C.

(57) ABSTRACT

A brake adjustment body is disposed in a direction orthogonal to turning shafts between a bending drive shaft and a lock operation shaft. The brake adjustment body is configured by including an intermediate member that abuts a cam portion of the lock operation shaft, and a brake member that applies to the bending drive shaft a pressure according to displacement of the intermediate member. The intermediate member has a shaft body portion and a cylindrical sliding portion screwed together, and by rotating the sliding portion in a state where the shaft body portion and the sliding portion are screwed together, the distance between a proximal end portion and a distal end portion of the intermediate member may be adjusted, and when fixing force on the bending drive shaft is reduced, the distance may be re-adjusted to restore the fixing force.

7 Claims, 10 Drawing Sheets

(58) Field of Classification Search
CPC ... A61B 1/0055; A61B 1/0056; A61B 1/0057; A61B 1/0058; A61B 1/008; A61B 34/30; A61B 34/32; A61B 34/35; A61B 34/37; A61B 34/70; A61B 34/71; A61B 34/72; A61B 2034/301–2034/306; A61B 2034/715; A61B 2017/003; A61B 2017/00305; A61B 2017/00309; A61B 2017/00314; A61B 2017/00318; A61B 2017/00323; A61B 2017/00327; A61B 2017/00331
USPC .......................................................... 600/149
See application file for complete search history.

(56) References Cited

FOREIGN PATENT DOCUMENTS

| JP | 2008-023064 A | 2/2008 |
| JP | 2012-249862 A | 12/2012 |
| JP | 2013-005996 A | 1/2013 |

OTHER PUBLICATIONS

Japanese Office Action dated Mar. 1, 2016 issued in JP 2015-561444.

* cited by examiner

BENDING OPERATION APPARATUS OF ENDOSCOPE, AND ENDOSCOPE

CROSS REFERENCE TO RELATED APPLICATION

This application is a continuation application of PCT/JP2015/062843 filed on Apr. 28, 2015 and claims benefit of Japanese Application No. 2014-169441 filed in Japan on Aug. 22, 2014, the entire contents of which are incorporated herein by this reference.

BACKGROUND OF THE INVENTION

1. Field of the Invention

The present invention relates to a bending operation apparatus of an endoscope including a bendable bending portion, and the endoscope.

2. Description of the Related Art

An endoscope including a bending portion configured to direct a distal end portion of an insertion section to a desired direction is widely used as an endoscope to perform observation, various treatments and the like by having an elongated insertion section inserted into a living body or the like. Generally, this type of endoscope has an operation section consecutively provided on a proximal portion side of the insertion section, and an operation of bending the bending portion is performed through a bending operation apparatus provided in the operation section.

As the bending operation apparatus, a structure which is configured to bend the bending portion by pulling or slackening an operation wire connected to the bending portion is widely used, and in this case, a rotating member such as a pulley or a sprocket is generally used to pull or slacken the operation wire.

Furthermore, generally, this type of bending operation apparatus is provided with a lock mechanism configured to restrict (brake) rotation of the rotating member with a predetermined amount of fixing force, and to fix (lock) the bending portion in a desired bent state. For example, Japanese Patent Application Laid-Open Publication No. 2008-23064 discloses a bending operation apparatus according to which, when a lock operation shaft is rotated around the shaft, a locking plate is eccentrically rotated to perform braking by coming into contact with and moving away from the outer circumferential surface of a pulley drive shaft.

A conventional lock mechanism as disclosed in Japanese Patent Application Laid-Open Publication No. 2008-23064 is configured to slow the operation of the pulley by pressing a friction member such as the locking plate against the pulley drive shaft to thereby lock a bending portion.

SUMMARY OF THE INVENTION

A bending operation apparatus of an endoscope according to an aspect of the present invention is a bending operation apparatus of an endoscope including an insertion section having a bendable bending portion and an operation section consecutively provided on a proximal end side of the insertion section, the bending operation apparatus including a base member disposed in the operation section, a first rotation shaft rotatably held by the base member and configured to rotate by a bending operation on the bending portion by an operator, a second rotation shaft provided side by side with the first rotation shaft and rotatably held by the base member, a cam portion provided in the second rotation shaft, configured to rotate in coordination with rotation of the second rotation shaft, and including an acting surface on an outer circumference, and a brake adjustment body formed to be adjustable in length from a proximal end portion to a distal end portion, the brake adjustment body being disposed between the acting surface of the cam portion and an outer circumferential portion of the first rotation shaft by adjusting the length, the distal end portion being configured to press against the outer circumferential portion of the first rotation shaft according to a rotation radius of the acting surface at a time of rotation of the cam portion.

An endoscope according to an aspect of the present invention includes the bending operation apparatus of the endoscope according to the aspect described above.

DETAILED DESCRIPTION OF THE PREFERRED EMBODIMENTS

Hereinafter, embodiments of the present invention will be described with reference to the drawings.

Figure 1:
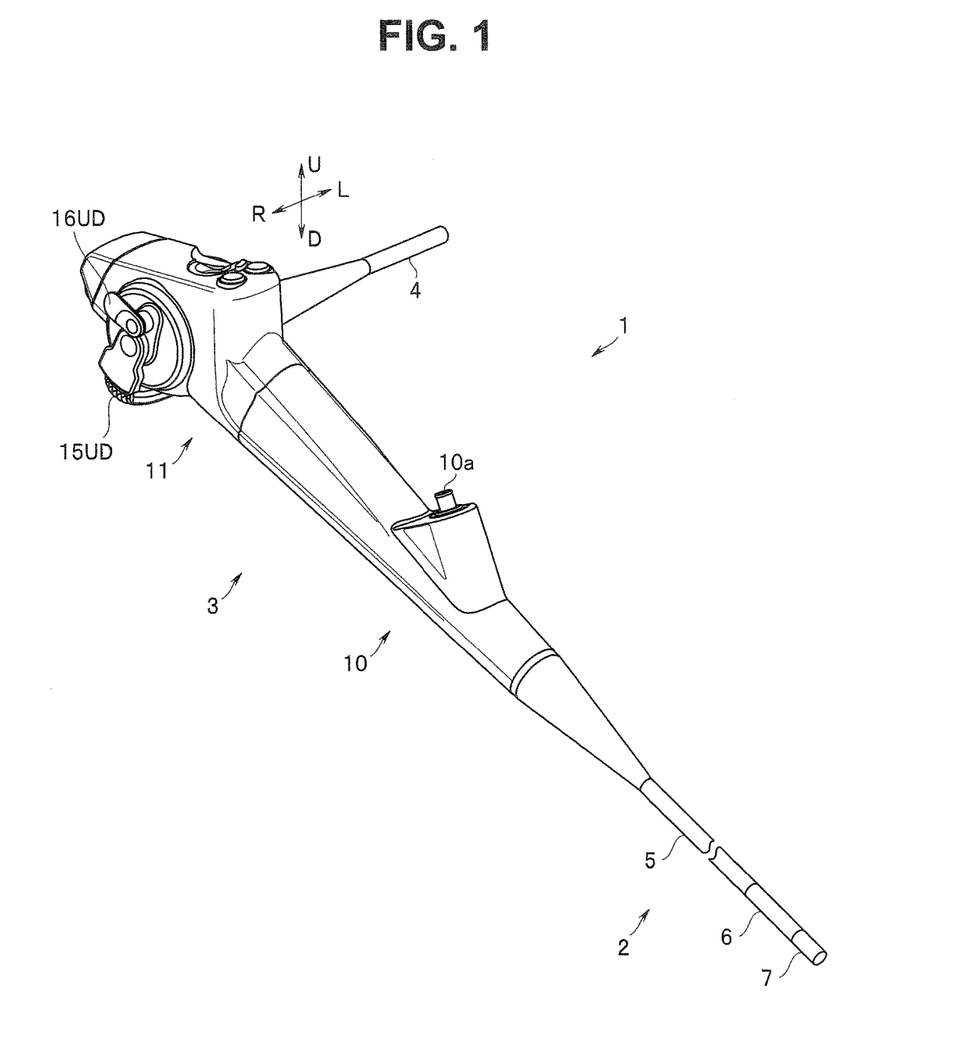
FIG. 1 is an external view of an endoscope according to a first embodiment of the present invention.

First, a first embodiment of the present invention will be described. As shown in FIG. 1, an endoscope 1 is configured by including an elongated insertion section 2, an operation section 3 which is consecutively provided on a proximal end of the insertion section 2, and a universal cord 4 extending from a proximal end side of the operation section 3.

A flexible tube portion 5, which is soft and flexible, a bending portion 6, and a distal end portion 7 are provided in the insertion section 2 in this order from the side of the operation section 3. Note that the insertion section 2 may be provided with a rigid portion instead of the flexible tube portion 5.

Bending operation wires 17UD, 17LR (see FIGS. 5 and 7) extending from the side of the operation section 3 are inserted through the flexible tube portion 5, and distal end portions of the bending operation wires 17UD, 17LR are connected to the bending portion 6. The bending operation wires 17UD, 17LR are capable of being pulled and slackened alternately by a bending operation mechanism portion 20UD, 20LR described later, and the bending portion 6 is thereby bent in an up-down (U-D) direction or a left-right (L-R) direction in FIG. 1, for example.

The operation section 3 is configured by including a grasping portion 10 which is consecutively provided on the proximal end of the insertion section 2, and an operation section main body 11 which is consecutively provided on a proximal portion side of the grasping portion 10. A treatment instrument channel opening portion 10*a* as an opening portion of a treatment instrument channel configured to allow insertion of various treatment instruments into the insertion section 2 is provided on a distal end side of the grasping portion 10.

Figure 2:
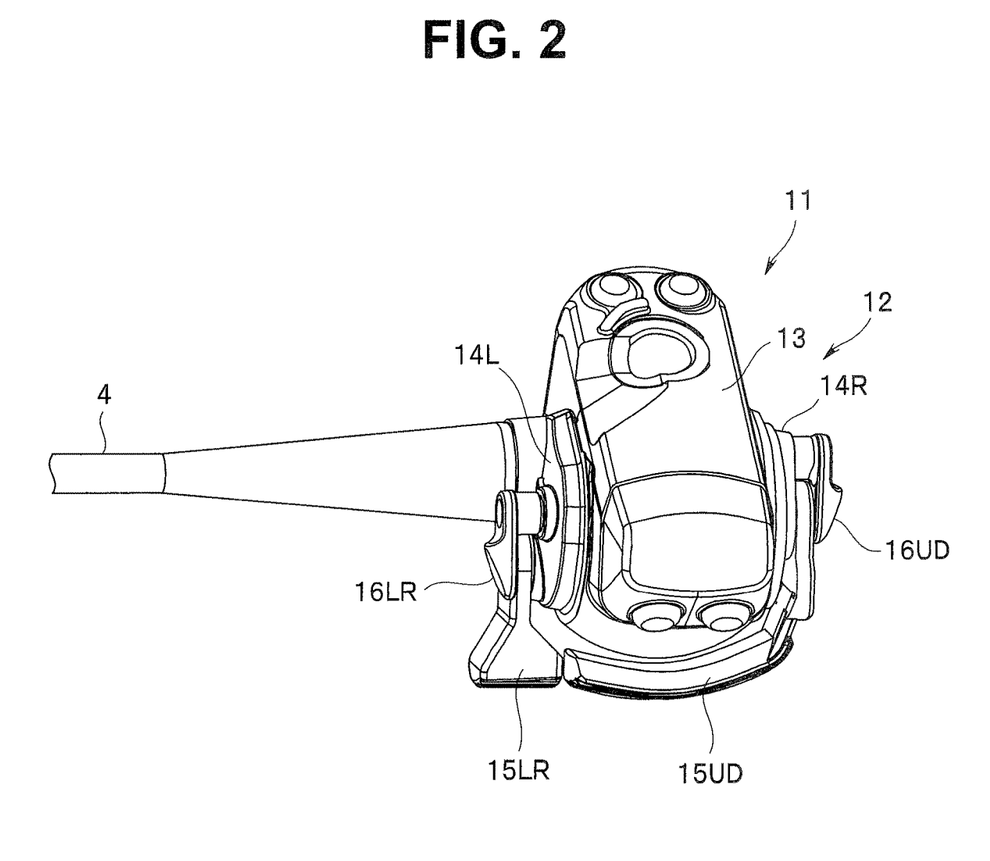
FIG. 2 is an explanatory view, according to the first embodiment, showing an operation section from a proximal end side.
Figure 3:
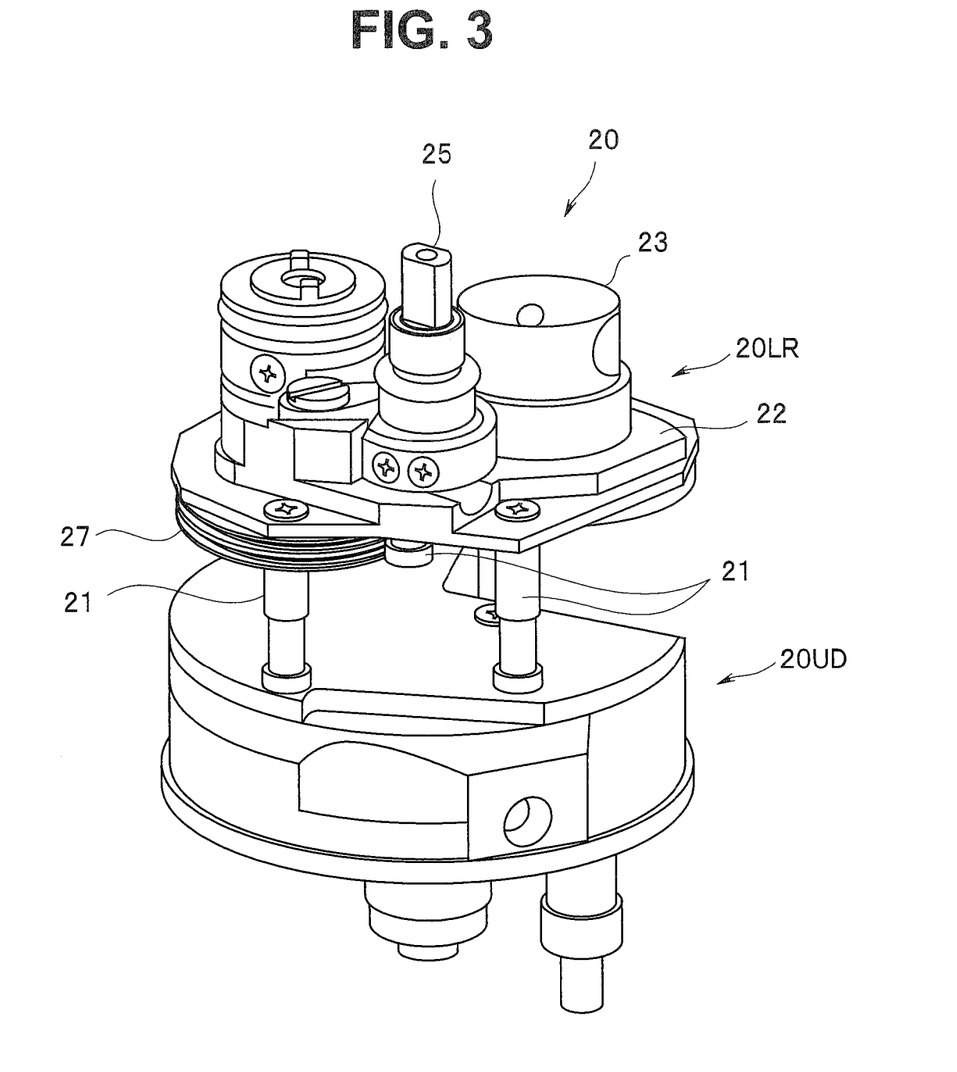
FIG. 3 is an explanatory view, according to the first embodiment, showing an arrangement of up-down and left-right bending operation mechanism portions.
Figure 4:
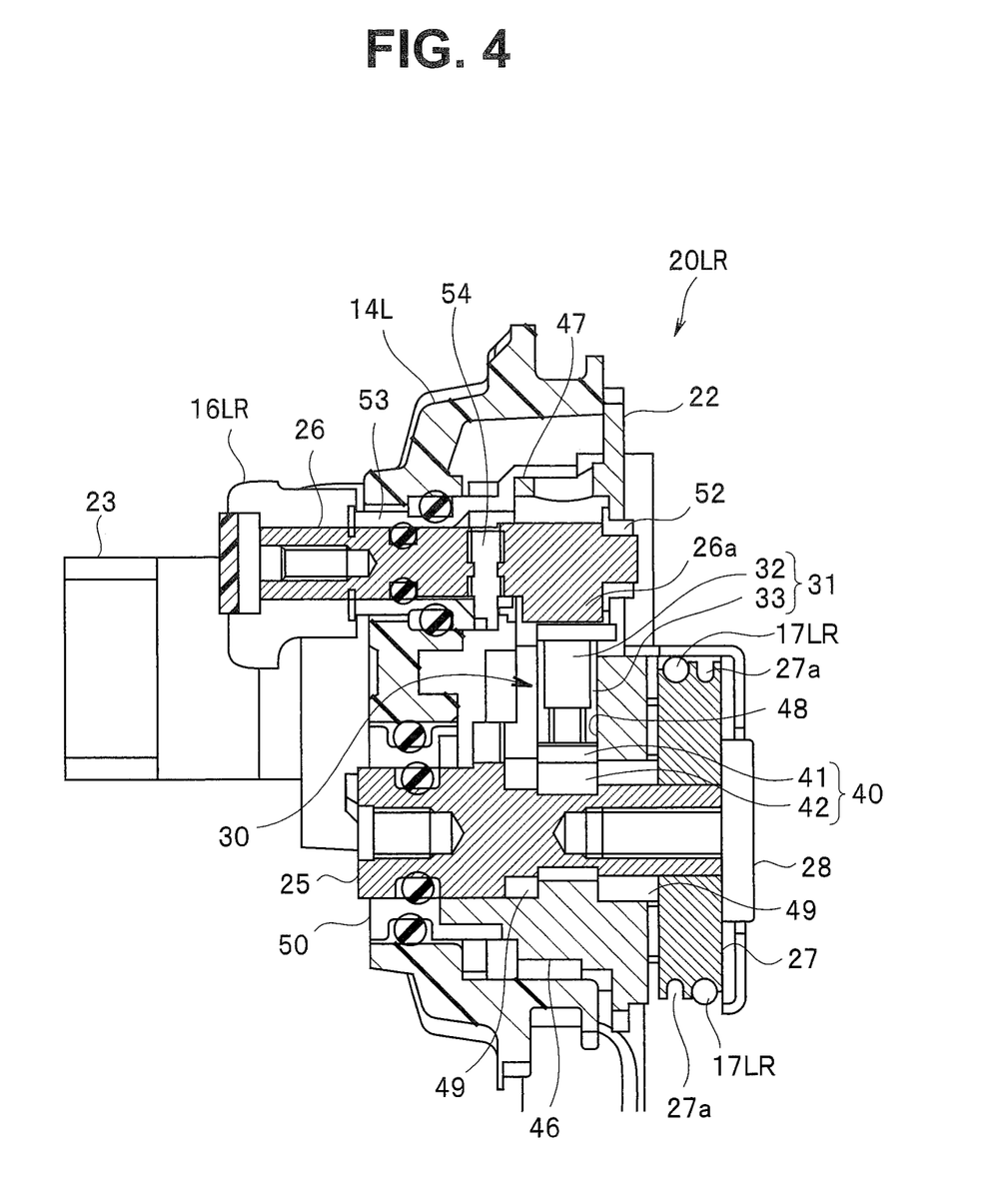
FIG. 4 is a cross-sectional view, according to the first embodiment, showing main portions of the bending operation mechanism portion.

The bending operation mechanism portion 20UD for up-down bending and the bending operation mechanism portion 20LR for left-right bending are disposed inside the operation section main body 11 (see FIGS. 3 and 4). Also, on the outside the operation section main body 11, bending operation levers 15UD, 15LR and bending lock levers 16UD, 16LR which are coupled to the bending operation mechanism portions 20UD, 20LR are swingably disposed, and also, operation switches and the like corresponding to various endoscopic functions are disposed (see FIGS. 1 and 2). Furthermore, a proximal end portion of the universal cord 4 is coupled to a side portion of the operation section main body 11.

Specifically, as shown in FIG. 2, an outer case 12 constituting the operation section main body 11 includes a case main body 13 including circular opening portions on both left and right sides, and outer covers 14L, 14R configured to block the opening portions. In the present embodiment, the bending operation mechanism portion 20UD for up-down bending is held inside the operation section main body 11 via the outer cover 14R on the right side, and the bending operation mechanism portion 20LR for left-right bending is held inside the operation section main body 11 via the outer cover 14L on the left side to which the universal cord 4 is coupled.

As shown in FIG. 3, the bending operation mechanism portion 20UD for up-down bending and the bending operation mechanism portion 20LR for left-right bending are arranged facing each other, and are coupled by three shaft-like joints 21 to form a bending operation apparatus 20. In the present embodiment, the bending operation mechanism portion 20LR for left-right bending is disposed on a base plate 22, which is a base member covered with the outer cover 14L, and is arranged next to a guide metal fitting 23 serving as a passage for guiding, into the universal cord 4, internal components such as a light guide configured to transmit illumination light, tubes and the like forming various channels, signal cables and the like.

According to such an arrangement, sizes and arrangement of structural members are more limited for the bending operation mechanism portion 20LR for left-right bending than for the bending operation mechanism portion 20UD for up-down bending, and as shown in FIG. 4, the bending operation mechanism portion 20LR for left-right bending has a more compact and unique configuration than in the past. In the following, the unique configuration of the bending operation mechanism portion 20LR for left-right bending will be described. The bending operation mechanism portion 20UD for up-down bending may have the same configuration as in the past, or may have the same configuration as that of the bending operation mechanism portion 20LR for left-right bending described below.

As shown in FIG. 4, the bending operation mechanism portion 20LR is configured by rotatably holding, at the base plate 22 disposed on the outer cover 14L side of the case main body 13, a bending drive shaft 25 serving as a first rotation shaft to which the bending operation lever 15LR is attached, and a lock operation shaft 26 serving as a second rotation shaft to which the bending lock lever 16LR is attached. The lock operation shaft 26 is arranged near the bending drive shaft 25, substantially in parallel to the bending drive shaft 25.

Figure 5:
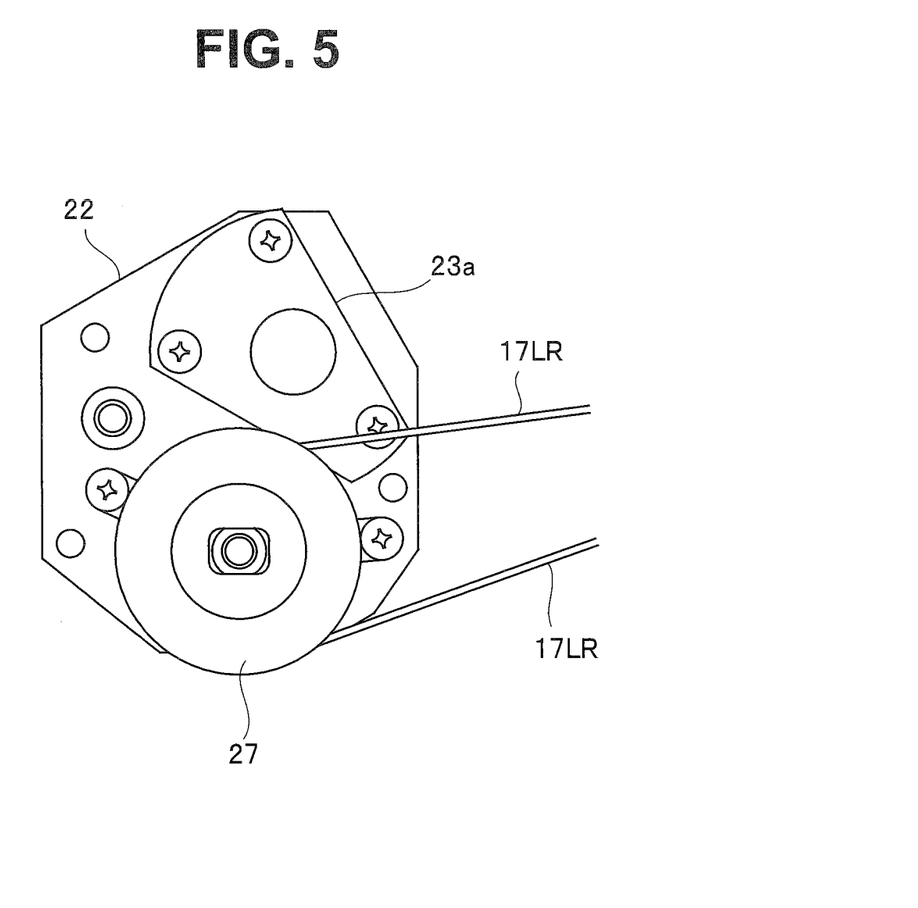
FIG. 5 is a plan view, according to the first embodiment, showing a base plate from a pulley side.

A protruding end, of the bending drive shaft 25, on the back surface side of the base plate 22 is formed to be rectangular, for example, and a pulley 27 configured to pull/slacken a pair of bending operation wires 17LR is fitted to the rectangular protruding end, and is retained by a screw 28. As shown in FIG. 5, the pulley 27 is arranged adjacent to a flange portion 23*a* of the guide metal fitting 23 attached to the base plate 22, and is formed as a pulley with a relatively small diameter to contribute to miniaturization of the operation section 3.

Figure 6:
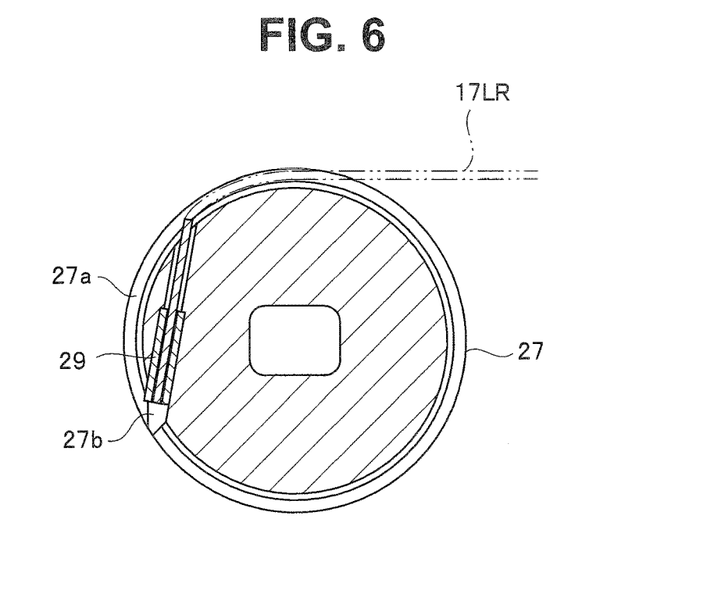
FIG. 6 is a cross-sectional view, according to the first embodiment, showing a fixing portion of a bending operation wire to a pulley.

The pulley 27 with a small diameter includes two groove portions 27*a*, and a wire end portion of one of the pair of bending operation wires 17LR and a wire end portion of the other of the pair are held by the respective groove portions 27*a*, respectively. Specifically, as shown in FIG. 6, a retaining portion 27*b* configured to retain the bending operation wire 17LR that is inserted is provided in each groove portion 27*a* of the pulley 27. For example, a wire stop 29 of stainless steel which is formed at a proximal end portion of the bending operation wire 17LR by a known swaging process or the like is accommodated in each retaining portion 27*b*, and is held by being soldered.

That is, conventionally, if a pulley is miniaturized, it is difficult to secure spaces for separately fixing respective end portions of a pair of bending operation wires. On the other hand, with the pulley 27 of the present embodiment including two groove portions 27*a*, the retaining portions 27*b* for wires are provided in the two groove portions 27*a*, respectively, and in spite of being small, the pulley may secure spaces for separately fixing the respective end portions of the pair of wires.

Figure 7:
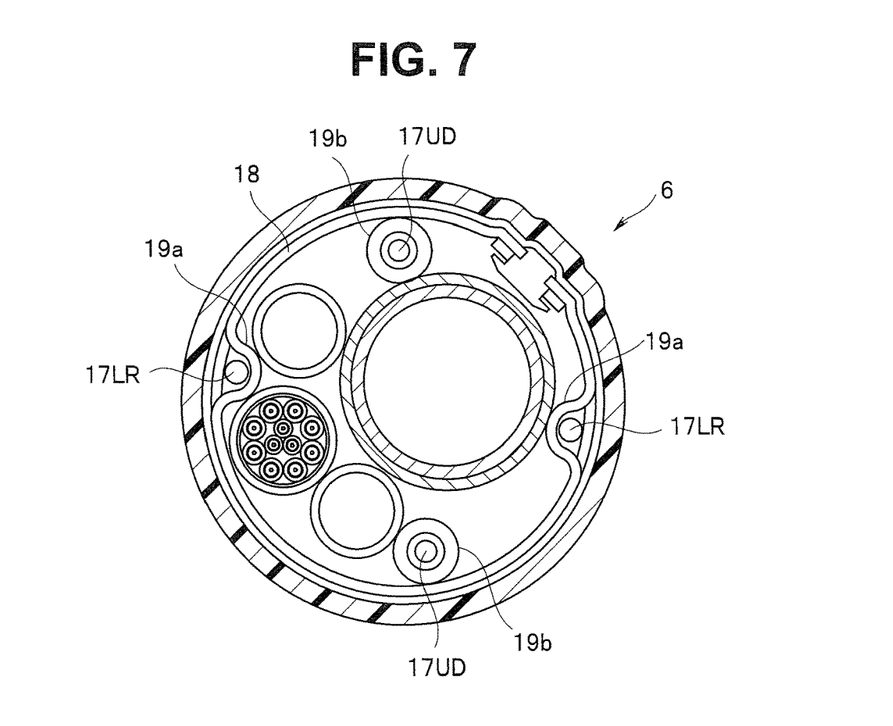
FIG. 7 is a cross-sectional view, according to the first embodiment, showing a wire guide of the bending operation wire.

Furthermore, the specification of the endoscope 1 of the present embodiment is such that a bending angle of the bending portion 6 is greater for the up-down (U-D) direction than for the left-right (L-R) direction. Accordingly, as shown in FIG. 7, two types of wire guides, i.e. wire guides 19*a* formed by lancing a pipe and wire guides 19*b* which are circular cylindrical members of another member fixed by brazing or the like, are mixedly present inside a bending piece 18 of the bending portion 6, and bending operation wires 17LR for left-right bending are inserted through the wire guides 19*a*, and the bending operation wires 17UD for up-down bending are inserted through the wire guides 19*b*.

The wire guides 19a obtained by lancing a pipe may reduce the height of protrusions in the inner diameter direction, and may reduce the filling rate of internal components. The tubular wire guides 19b formed of another member may have end portions rounded in advance, and thus, do not damage the internal components. Accordingly, by using the wire guides 19a obtained by lancing a pipe for the bending operation wires LR for left-right bending with small bending angle, and using the tubular wire guides 19b formed of another member for the bending operation wires 17UD for up-down bending with large bending angle, the filling rate of internal components may be increased without damaging the internal components.

Figure 8:
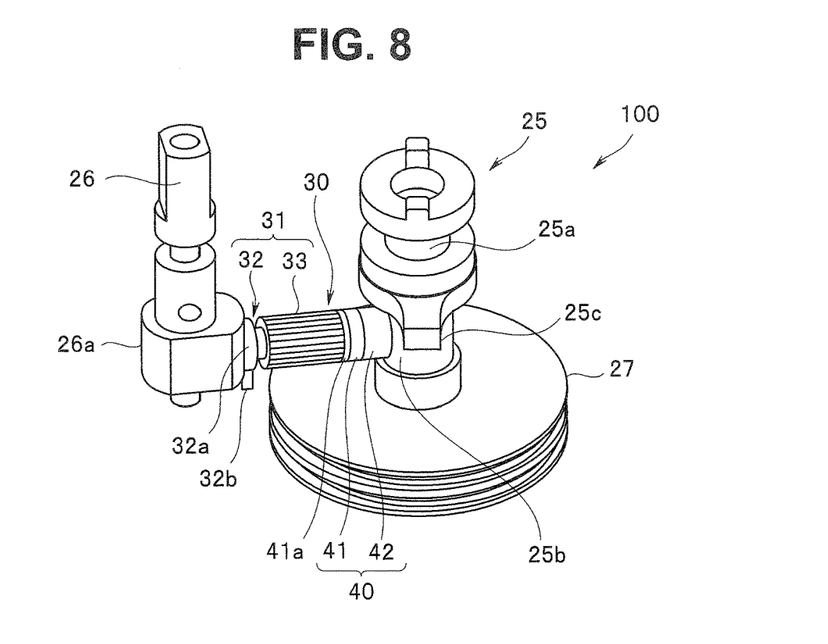
FIG. 8 is a perspective view, according to the first embodiment, showing main portions of a lock mechanism portion.

Next, the lock operation shaft 26 arranged adjacent to the bending drive shaft 25 of the pulley 27 will be described. As shown in FIG. 8, the lock operation shaft 26 constitutes, together with a brake adjustment body 30 which is interposed in a direction orthogonal to turning shafts between the bending drive shaft 25 and the lock operation shaft 26, main portions of a lock mechanism portion 100 configured to lock rotation of the pulley 27.

A cam portion 26a including, at an outer circumference, an acting surface that abuts the brake adjustment body 30 is provided in a proximal end portion, of the lock operation shaft 26, on the side of the base plate 22. The cam portion 26a is formed to include a turning shaft that is eccentric by a predetermined amount from the turning shaft of the lock operation shaft 26, and when the cam portion 26a rotates in coordination with rotation of the lock operation shaft 26, the acting surface abutting the brake adjustment body 30 is displaced in the direction orthogonal to the turning shaft of the lock operation shaft 26.

The brake adjustment body 30 is configured by including an intermediate member 31 whose proximal end portion abuts the acting surface of the cam portion 26a, and a brake member 40 which abuts a distal end portion of the intermediate member 31. The intermediate member 31 further includes a shaft body portion 32 including a flange portion 32a serving as the proximal end portion abutting the acting surface of the cam portion 26a, and a sliding portion 33 including the distal end portion abutting the brake member 40, the sliding portion 33 being slidably accommodated in a brake adjustment body accommodating portion 48 (see FIG. 9), described later, of the base plate 22.

Below the neck of the flange portion 32a of the shaft body portion 32 is a screw portion provided with a male screw, and the screw portion of the male screw is screwed to a female screw inside the sliding portion 33 to be coupled and to form the intermediate member 31. Also, the brake member 40 includes a first surface portion 41 which abuts the distal end portion of the intermediate member 31, and a second surface portion 42 which is disposed so as to be able to come into contact with an outer circumferential portion of the bending drive shaft 25.

Specifically, the intermediate member 31 includes the male screw on the outer circumference of the shaft of the shaft body portion 32, and achieves integration by having the male screw screwed into the female screw provided inside the cylindrical sliding portion 33. Knurling is applied to the outer circumferential surface of the sliding portion 33, and by turning the knurled surface of the sliding portion 33 by tweezers or the like in a state where the shaft body portion 32 and the sliding portion 33 are screwed together, the distance between the proximal end portion and the distal end portion of the intermediate member 31 may be changed and adjusted.

Note that a protrusion 32b protrudes from the flange portion 32a of the shaft body portion 32 in a radial direction. As will be described later, when the intermediate member 31 is assembled with the base plate 22, the protrusion 32b is engaged with the base plate 22, and relative turning of the shaft body portion 32 and the sliding portion 33 at the time of forward-backward movement of the intermediate member 31 is prevented. Also, the knurling on the outer circumference of the sliding portion 33 is shown to be straight knurling, but it may also be diagonal knurling or diamond knurling.

Meanwhile, the brake member 40 includes the first surface portion 41 which is a circular plate made of a flexible material such as rubber, and the second surface portion 42 which is columnar and which is made of a rigid material such as metal. The first surface portion 41 transmits pressure to the second surface portion 42 while deforming due to displacement of the intermediate member 31. The second surface portion 42 presses the bending drive shaft 25 with the force from the intermediate member 31 transmitted via the first surface portion 41.

Note that, in the present embodiment, a circular plate 41a of a rigid material such as metal is interposed between the first surface portion 41 of a flexible material and a distal end surface of the sliding portion 33 of the intermediate member 31. This is because the female screw inside the sliding portion 33 is a through screw, and the first surface portion 41 of a flexible member has to be prevented from being damaged and deteriorated by being placed inside the hole of the through screw. In the case where the female screw inside the sliding portion 33 is not a through screw, the circular plate 41a is not necessary.

Furthermore, the bending drive shaft 25 is formed from a rigid portion 25b whose outer circumferential portion, which can come into contact with the brake member 40, at least is made of a rigid material such as metal, in contrast to a turning shaft main body 25a serving as a rotation shaft, and to reduce friction due to contact with the brake member 40, grease or the like is desirably applied on the contact surface.

Figure 9:
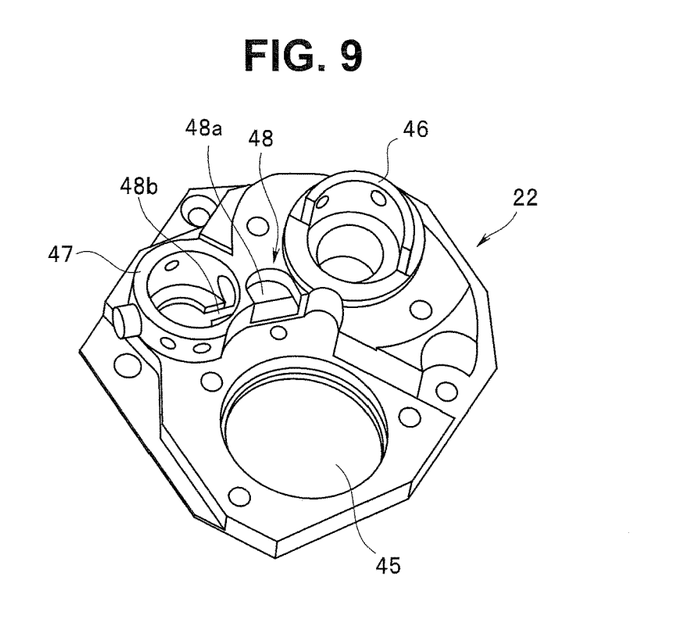
FIG. 9 is a perspective view of the base plate according to the first embodiment.
Figure 10:
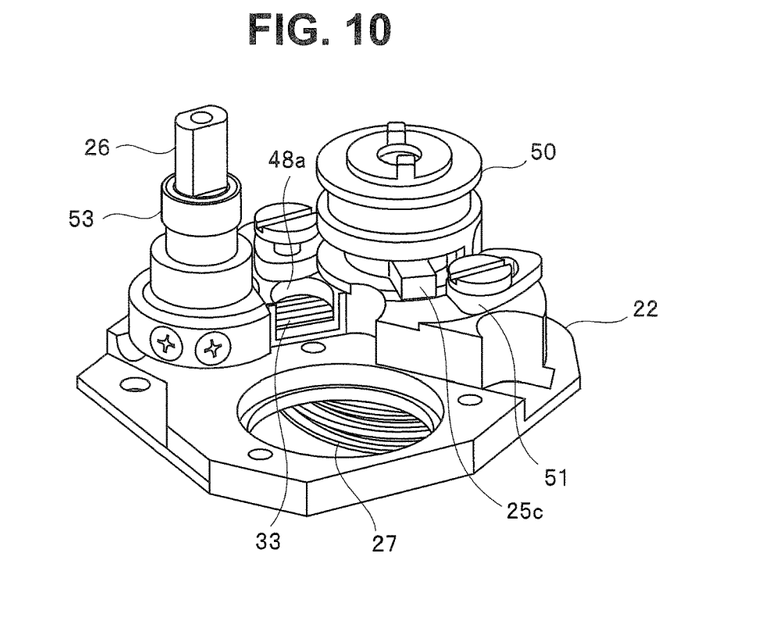
FIG. 10 is a perspective view, according to the first embodiment, showing a state in which the lock mechanism portion is assembled with the base plate.

The bending drive shaft 25, the lock operation shaft 26, and the brake adjustment body 30 described above are assembled to the base plate 22. As shown in FIG. 9, the base plate 22 includes a circular cylindrical first boss portion 46 which is adjacent to an opening portion 45 where the guide metal fitting 23 is to be mounted and which is configured to hold the bending drive shaft 25, a circular cylindrical second boss portion 47 which is configured to hold the lock operation shaft 26, and a brake adjustment body accommodating portion 48 which is shaped as a horizontal hole and which is configured to communicate between the first boss portion 46 and the second boss portion 47 and to accommodate the brake adjustment body 30.

As shown in FIG. 4 and FIGS. 8 to 11, the bending drive shaft 25 is inserted in the first boss portion 46 of the base plate 22, and is rotatably held via upper and lower bearings 49 of resin or the like. The outer cover 14L of the case main body 13 is mounted on the distal end side of the bending drive shaft 25 via a turning shaft cover 50, and the pulley 27 is fixedly installed at the protruding end on the back surface side of the base plate 22. The rigid portion 25b, of the bending drive shaft 25, where the brake member 40 is to abut is exposed from inside of the first boss portion 46 to the brake adjustment body accommodating portion 48.

Note that a tongue-shaped turning restriction portion 25c extends in a radial direction from a part of the bending drive shaft 25, between the first boss portion 46 and the turning shaft cover 50, and the rotation range of the bending drive shaft 25 is restricted to the range up to abutting of the turning restriction portion 25c against a stopper 51 mounted near the first boss portion 46 of the base plate 22.

Also, the lock operation shaft 26 is inserted in the second boss portion 47 of the base plate 22, and is rotatably held via a bearing 52 of resin or the like. The distal end side of the lock operation shaft 26 is supported by the outer cover 14L of the case main body 13 via a turning shaft cover 53. Note that a groove allowing a turning restriction pin 54 fixedly installed to the lock operation shaft 26 to move in the circumferential direction is provided in the turning shaft cover 53 of the lock operation shaft 26, and the rotation range of the lock operation shaft 26 is restricted to the range of the groove.

On the other hand, the brake adjustment body 30 including the intermediate member 31 and the brake member 40 is accommodated inside the brake adjustment body accommodating portion 48 communicating between the first boss portion 46 and the second boss portion 47. Here, the brake adjustment body 30 is arranged in such a way that the distal end side of the brake member 40 abuts the bending drive shaft 25 and the proximal end side (the flange portion 32a) of the shaft body portion 32 constituting the intermediate member 31 is allowed to abut the cam portion 26a of the lock operation shaft 26 inside the second boss portion 47.

Also, the brake adjustment body accommodating portion 48 is provided with a window portion 48a which is opened by cutting out a part of a circular cylindrical portion slidably accommodating the sliding portion 33 of the intermediate member 31 of the brake adjustment body 30, and an outer surface (knurled surface) of the sliding portion 33 of the intermediate member 31 is exposed from the window portion 48a. Moreover, a groove-shaped cut-out portion 48b is opened to a communication portion of the second boss portion 47 to the brake adjustment body accommodating portion 48, toward the brake adjustment body accommodating portion 48, and the protrusion 32b of the shaft body portion 32 screwed to the sliding portion 33 is placed in the cut-out portion 48b.

Figure 11:
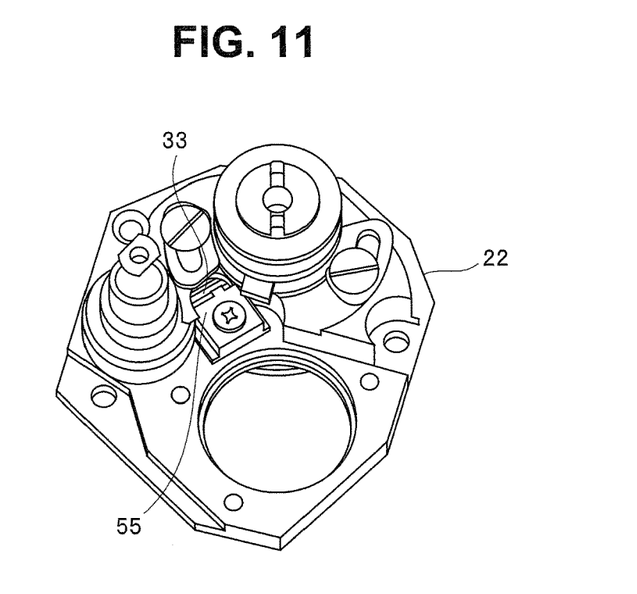
FIG. 11 is a perspective view, according to the first embodiment, showing a state in which a turning restriction member is attached in FIG. 10.

Moreover, as shown in FIG. 11, after the brake adjustment body 30 is assembled with the brake adjustment body accommodating portion 48 of the base plate 22, a claw-shaped turning restriction member 55 configured to press the outer surface (knurled surface) of the sliding portion 33 exposed from the window portion 48a is screwed to near the window portion 48a of the brake adjustment body accommodating portion 48. This allows relative rotation of the shaft body portion 32 and the sliding portion 33 at the time of forward-backward movement of the intermediate member 31 to be reliably prevented.

Next, braking (locking) and releasing of the bending drive shaft 25 (the pulley 27) by the lock mechanism portion 100 described above will be described.

After operating the bending operation lever 15LR and rotating the pulley 27, and bending the bending portion 6 to a desired angle via the bending operation wires 17LR, a surgeon or the like operates the bending lock lever 16LR to maintain the state, and the lock operation shaft 26 is rotated through the operation input. Rotation of the lock operation shaft 26 causes the acting surface of the cam portion 26a to abut the shaft body portion 32 of the intermediate member 31 of the brake adjustment body 30 and to cause the brake adjustment body 30 to move toward the bending drive shaft 25, and the brake member 40 of the brake adjustment body 30 abuts the outer circumferential portion of the bending drive shaft 25.

When the lock operation shaft 26 is further rotated in this state, the first surface portion 41 of the brake member 40 deforms under pressure according to the displacement of the intermediate member 31, and transmits pressure of a predetermined force to the second surface portion 42. The second surface portion 42 applies the pressure from the intermediate member 31 transmitted via the first surface portion 41 to the bending drive shaft 25. Rotation of the bending drive shaft 25 is thereby braked (locked) by the frictional force caused between the second surface portion 42 and the bending drive shaft 25, and the bending portion 6 may be fixed at a bending angle according to the turning angle of the bending drive shaft 25.

To release the fixation of the bending portion 6, the bending lock lever 16LR is rotated in the reverse direction, and rotation is performed so as to separate the acting surface of the cam portion 26a of the lock operation shaft 26 from the shaft body portion 32 of the brake adjustment body 30. This allows the second surface portion 42 of the brake member 40 to be separated from the outer circumferential surface of the bending drive shaft 25, and braking (locking) of the bending drive shaft 25 (the pulley 27) is released.

If braking (locking) and releasing of the bending drive shaft 25 (the pulley 27) by the lock mechanism portion 100 are repeated, the acting surface of the cam portion 26a of the lock operation shaft 26, each abutting portion of the brake adjustment body 30 (the shaft body portion 32 of the intermediate member 31, the second surface portion 42 of the brake member 40), the rigid portion 25b of the bending drive shaft 25 and the like may become worn, and the fixing force on the bending drive shaft 25 is possibly reduced. Conventionally, in such a case, to secure sufficient fixing force, parts have to be replaced, and the repair cost is increased.

On the other hand, in the present embodiment, even if respective parts constituting the lock mechanism portion 100 become worn, sufficient fixing force may be restored simply by adjusting the intermediate member 31, without having to replace the parts.

That is, if each abutting portion is worn, the positional relationship of the second surface portion 42 of the brake member 40 and the outer circumferential surface (the rigid portion 25b) of the bending drive shaft 25 is changed in the direction of causing a gap between the two, and it becomes difficult for the second surface portion 42 of the brake member 40 to appropriately press against the outer circumferential surface (the rigid portion 25b) of the bending drive shaft 25. Accordingly, re-adjustment may be performed by adjusting the intermediate member 31 of the brake adjustment body 30 to be longer in the axial direction so that the second surface portion 42 of the brake member 40 may appropriately press against the outer circumferential surface (the rigid portion 25b) of the bending drive shaft 25 as in the initial state.

Specifically, the outer cover 14L is removed from the case main body 13 of the operation section 3, and the outer surface (knurled surface) of the sliding portion 33 of the intermediate member 31 is exposed to outside from the window portion 48a opened to the brake adjustment body accommodating portion 48 of the base plate 22. Then, an operator rotates the sliding portion 33 by hooking tweezers to the knurling on the outer surface of the sliding portion 33, for example.

Although the sliding portion 33 is rotated, the shaft body portion 32 screwed to the sliding portion 33 has the protrusion 32b placed in the cut-out portion 48b of the base plate 22 and rotation of the shaft body portion 32 is prevented. As a result, by rotating the sliding portion 33, the coupling length of the sliding portion 33 and the shaft body portion 32 may be adjusted, and the length of the entire brake adjustment body 30 in the axial direction may be adjusted to be longer so that the second surface portion 42 of the brake member 40 may be adjusted to appropriately press against the outer circumferential surface (the rigid portion 25b) of the bending drive shaft 25.

As described above, according to the present embodiment, a braking force is transmitted from the lock operation shaft 26 to the bending drive shaft 25 via the intermediate member 31 whose length in the axial direction can be adjusted, and thus, even if the fixing force for fixing the bending portion 6 in a desired bent state is reduced due to wear or the like of each member caused by repeated use, sufficient fixing force may be restored simply by re-adjusting the length of the intermediate member 31 in the axial direction by simple adjustment, without having to replace the parts.

Next, a second embodiment of the present invention will be described. In the second embodiment, the intermediate member 31 constituting the brake adjustment body 30 is changed, and due to the change of the intermediate member 31, the brake adjustment body accommodating portion 48 of the base plate 22 is also slightly changed.

Figure 12:
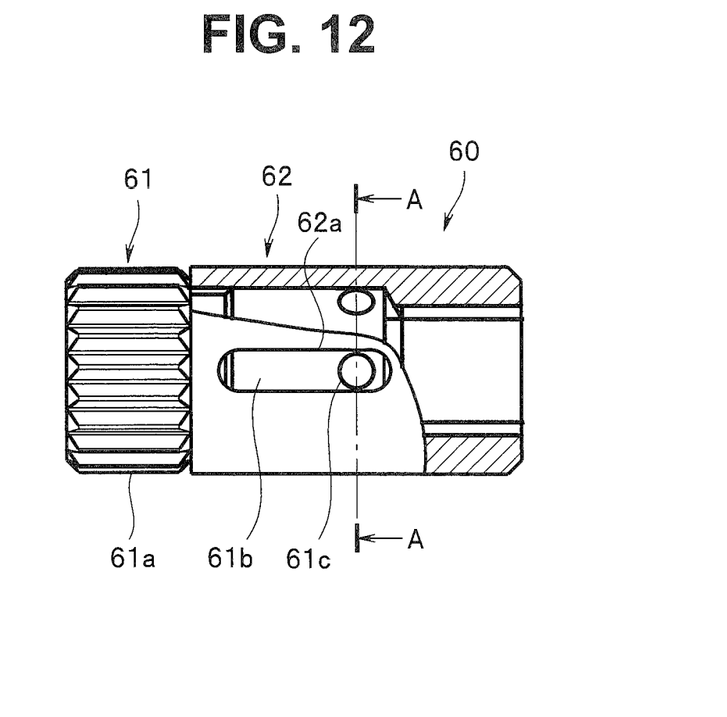
FIG. 12 is an explanatory view of a brake adjustment body according to a second embodiment of the present invention.

The intermediate member 31 in the first embodiment has the length in the axial direction adjusted by rotation of the sliding portion 33 with respect to the shaft body portion 32, but in the second embodiment, the length in the axial direction is adjusted for an intermediate member 60 formed from a shaft body portion 61 and a sliding portion 62 as shown in FIG. 12 by rotation of the shaft body portion 61.

Figure 13:
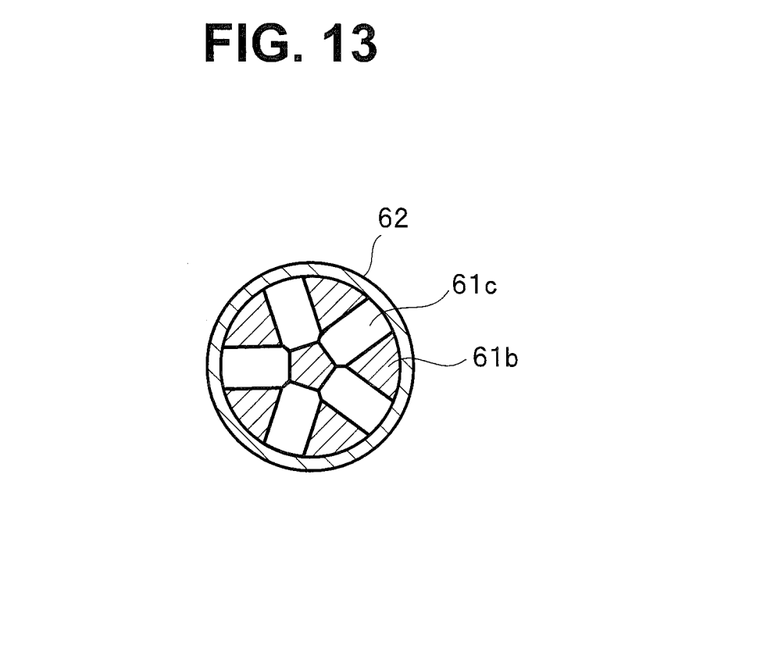
FIG. 13 is a cross-sectional view, according to the second embodiment, along line A-A in FIG. 12.

That is, the shaft body portion 61 includes a flange portion 61a serving as a proximal end portion which is to abut the acting surface of the cam portion 26a of the lock operation shaft 26, and a circular cylindrical main body portion 61b which is formed over a predetermined length below the neck of the flange portion 61a. Knurling (in FIG. 12, parallel knurling) is applied to an outer circumferential surface of the flange portion 61a, and a male screw is formed on a distal end side of the main body portion 61b. Moreover, a plurality of small holes 61c having predetermined depth in the radial direction are formed on an outer circumferential surface of the main body portion 61b, as shown in FIG. 13.

Meanwhile, the sliding portion 62 is formed into a circular cylindrical shape that slidably accommodates the main body portion 61b of the shaft body portion 61, and a female screw into which the male screw of the main body portion 61b is to be screwed is formed inside the distal end side of the sliding portion 62. A long hole 62a which is groove-shaped is opened in the axial direction on an outer circumferential surface of the sliding portion 62, and the small hole 61c of the shaft body portion 61 may be exposed from the long hole 62a.

Figure 14:
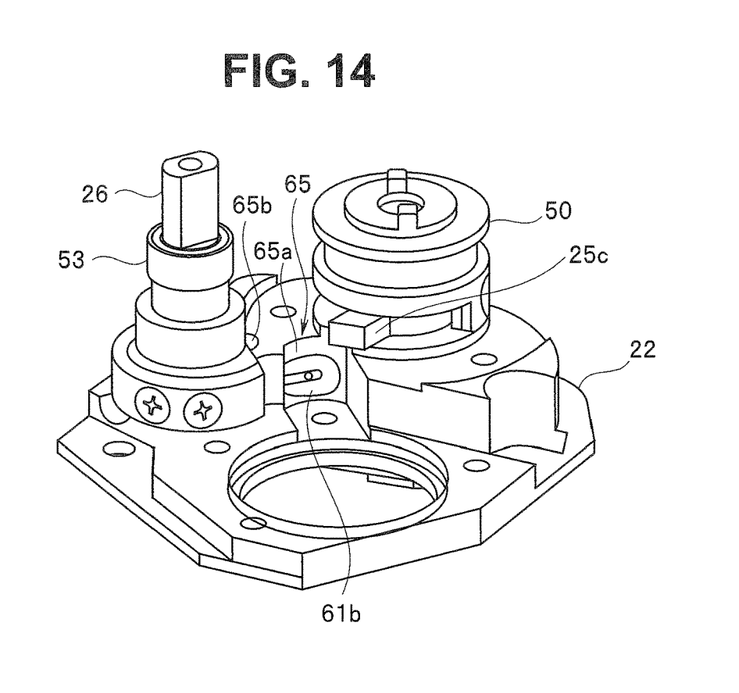
FIG. 14 is a perspective view, according to the second embodiment, showing the brake adjustment body assembled with a base plate.

A brake adjustment body accommodating portion 65 of the base plate 22 accommodating such an intermediate member 60 includes a first window portion 65a like that of the brake adjustment body accommodating portion 48 in the first embodiment, but dispenses with the groove-shaped cut-out portion 48b where the protrusion 32b of the shaft body portion 32 is to be placed, according to the change from the shaft body portion 32 in the first embodiment to the shaft body portion 61 in the second embodiment, and instead, a second window portion 65b exposing a part of an outer circumferential surface of the flange portion 61a of the shaft body portion 61 is opened.

In the second embodiment, in the case of re-adjusting the braking force of the bending drive shaft 25 (the pulley 27), the outer cover 14L is removed from the case main body 13 of the operation section 3, and the sliding portion 62 is exposed from the first window portion 65a of the brake adjustment body accommodating portion 65 of the base plate 22, and also, the flange portion 61a of the shaft body portion 61 is exposed from the second window portion 65b.

Then, a tool such as a pin is hooked to the knurling on the outer circumference of the flange portion 61a to rotate the shaft body portion 61, and the length of the intermediate member 60 in the axial direction (the coupling length of the shaft body portion 61 and the sliding portion 62) is adjusted. This allows the fixing force on the bending drive shaft 25 which is reduced by wear of each part may be restored by adjusting the length of the intermediate member 60 in the axial direction, and appropriate fixing force may be maintained.

Figure 15:
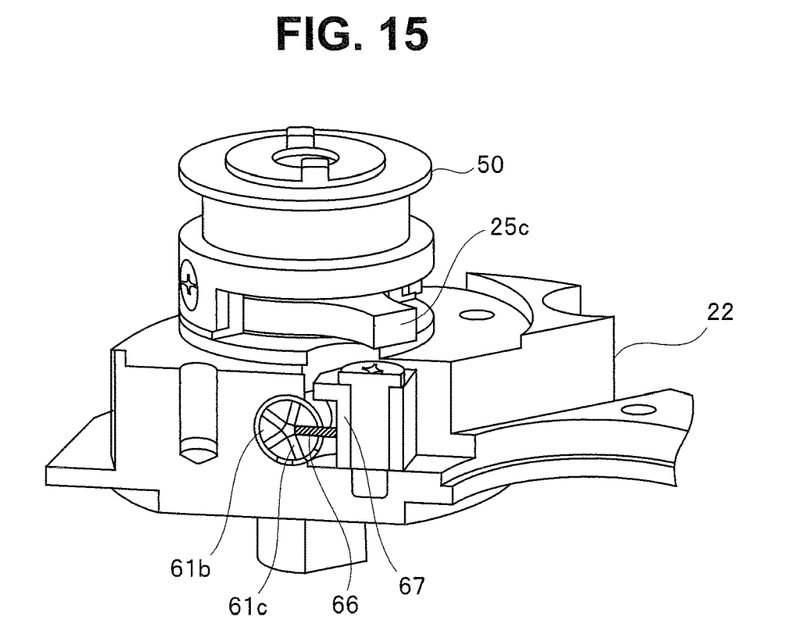
FIG. 15 is a perspective view, according to the second embodiment, showing a state in which a turning restriction member is attached to the brake adjustment body.

As shown in FIG. 15, after the length of the intermediate member 60 in the axial direction is adjusted, a pin 66 for preventing rotation is inserted into the small hole 61c of the main body portion 61b from the first window portion 65a via the long hole 62a of the sliding portion 62, and the claw-shaped turning restriction member 67 which is configured to restrict rotation of the pin 66 is screwed. This allows relative rotation of the shaft body portion 61 and the sliding portion 62 at the time of forward-backward movement of the intermediate member 60 to be reliably prevented. Note that the pin 66 for preventing rotation is not mounted before the adjustment but is mounted after the adjustment is completed.

Also in the second embodiment, a braking force is transmitted from the lock operation shaft 26 to the bending drive shaft 25 via the intermediate member 60 whose length in the axial direction can be adjusted, and thus, even if the fixing force for fixing the bending portion 6 in a desired bent state is reduced due to wear or the like of each member caused by repeated use, sufficient fixing force may be restored, as in the first embodiment, simply by re-adjusting the length of the intermediate member 60 in the axial direction by simple adjustment, without having to replace the parts.

What is claimed is:

1. A bending operation apparatus for use in an operation section of an endoscope, where the endoscope includes an insertion section having a bendable bending portion and the operation section consecutively provided on a proximal end side of the insertion section, the bending operation apparatus comprising:
   a base disposed in the operation section;
   a first rotation shaft rotatably supported by the base, the first rotation shaft being configured to bend the bending portion when the first rotation shaft is rotated;
   a second rotation shaft provided rotatably supported by the base at a position adjacent to the first rotation shaft;
   a cam provided in the second rotation shaft, the cam being configured to rotate with rotation of the second rotation shaft, the cam including an acting surface on an outer circumference of the cam; and
   a brake having a rigid portion with an adjustable length in a direction between the acting surface of the cam and an outer circumferential portion of the first rotation shaft, an end of the rigid portion being configured to press against the outer circumferential portion of the first rotation shaft upon rotation of the second rotation shaft;
   wherein the rigid portion is configured to change the length in the direction between the acting surface of the cam and the outer circumferential portion of the first rotation shaft by rotation of the rigid portion.

2. The bending operation apparatus of the endoscope according to claim 1, wherein the brake further includes a flexible portion that is deformable by a force of the pressing and abuts against the end of the rigid portion.

3. The bending operation apparatus according to claim 1, wherein the outer circumferential portion of the first rotation shaft includes a rotation shaft main body portion having a brake portion fixed to an outer circumference of the rotation shaft main body portion, the rigid portion being configured to come into contact with the brake.

4. The endoscope according to claim 1, wherein the operation section having a removable outer cover corresponding to a position of the rigid portion disposed within the operation section for accessing the rigid portion to change the length of the rigid portion.

5. The endoscope according to claim 1, wherein the rotation of the rigid portion is about an axis parallel to the direction between the acting surface of the cam and the outer circumferential portion of the first rotation shaft.

6. The endoscope according to claim 5, wherein the rigid portion comprises:
   a cylinder, an inside of which has a female thread; and
   an inner shaft, an outside of which has a male thread matingly engaging with the female thread,
   wherein an axis of the female thread and the male thread is along the direction between the acting surface of the cam and the outer circumferential portion of the first rotation shaft.

7. An endoscope comprising a bending operation apparatus of an endoscope according to claim 1.

* * * * *

UNITED STATES PATENT AND TRADEMARK OFFICE
CERTIFICATE OF CORRECTION

PATENT NO. : 10,085,623 B2
APPLICATION NO. : 15/260503
DATED : October 2, 2018
INVENTOR(S) : Itaru Osaki Page 1 of 1

It is certified that error appears in the above-identified patent and that said Letters Patent is hereby corrected as shown below:

In the Claims

Column 11, Claim 2, Line 3 reads:
2. The bending operation apparatus of the endoscope
Should read:
2. The bending operation apparatus Signed and Sealed this
Twenty-eighth Day of May, 2019

Andrei Iancu
*Director of the United States Patent and Trademark Office*